United States Patent [19]

Biebricher et al.

[11] 4,177,038

[45] Dec. 4, 1979

[54] METHOD FOR THE PRODUCTION OF A VEHICLE SUBSTANCE WHICH IS CAPABLE OF COVALENT BONDING WITH BIOLOGICALLY ACTIVE MATTER

[75] Inventors: Christof Biebricher, Adelebsen; Rüdiger Luce, Herzberg, both of Fed. Rep. of Germany

[73] Assignee: Max-Planck-Gesellschaft zur Förderung der Wissenschafen e.V., Göttingen, Fed. Rep. of Germany

[21] Appl. No.: 797,677

[22] Filed: May 17, 1977

[30] Foreign Application Priority Data

May 18, 1976 [DE] Fed. Rep. of Germany ....... 2621974

[51] Int. Cl.² .................... D06M 13/42; C08B 15/06; C08B 37/02
[52] U.S. Cl. ......................................... 8/192; 435/179; 435/178; 435/181; 525/123; 536/51; 8/DIG. 11
[58] Field of Search ....... 195/63, 68; 8/192, DIG. 11; 526/23, 49; 536/51, 1

[56] References Cited

U.S. PATENT DOCUMENTS

| | | | |
|---|---|---|---|
| 3,574,062 | 4/1971 | Sato | 195/63 |
| 3,672,955 | 6/1972 | Stanley | 195/68 |
| 3,705,084 | 12/1972 | Reynolds | 195/63 |
| 3,905,923 | 9/1975 | Klug | 195/DIG. 11 |
| 3,929,574 | 12/1975 | Wood et al. | 195/63 X |
| 3,947,352 | 3/1976 | Cuatrecasas et al. | 195/63 |
| 3,950,222 | 4/1976 | Takasaki | 195/68 |
| 4,063,017 | 12/1977 | Tsao et al. | 195/63 X |

*Primary Examiner*—Lionel M. Shapiro
*Attorney, Agent, or Firm*—Browdy and Neimark

[57] ABSTRACT

Process for preparing a vehicle substance capable of covalent bonding with biological material, especially enzymes, by reacting a matrix containing —OH or $NH_2$ groups with an organic diisocyanate under anhydrous conditions. The distance between the matrix and biological material may be extended by a stepwise reaction of the matrix with an organic diisocyanate, and organic spacer containing two or more —OH and/or $NH_2$ groups and again with an organic diisocyanate. The coupling of the vehicle material with biological material takes place in buffered aqueous solution.

26 Claims, 8 Drawing Figures

METHOD FOR THE PRODUCTION OF A VEHICLE SUBSTANCE WHICH IS CAPABLE OF COVALENT BONDING WITH BIOLOGICALLY ACTIVE MATTER

The invention is concerned with the production of a vehicle substance which is capable of covalent bonding with biologically active matter, and is formed from at least a vehicle preferably consisting of several —NH$_2$ or —OH groups and at least one bonding agent having at least two reactive groups. The invention moreover relates to a vehicle substance comprising at least one reactive group capable of immobilising biologically active matter, especially enzymes, and an agent which contains a biologically active substance which is immobilised by a vehicle substance.

The following terms are defined as follows for better understanding of the invention:

A "vehicle" is a starting material, for example cellulose, agarose, dextranes or the like, the essential feature being that the vehicle comprises NH$_2$ or OH-groups. In case a vehicle does not contain these groups they have to be made available in a preliminary reaction.

A "bonding agent" is a substance capable of adding biological matter or of condensing with the same. On the other hand, the bonding agent establishes the link with the vehicle, either directly or indirectly.

A "coupling agent" is a substance which always establishes a direct link with the vehicle. It may therefore be a "bonding agent". It is common to bonding agents and coupling agents that either may comprise two reactive groups.

A "spacer" is a chemical compound which generally contains two or several groups capable of reaction so that it can form a link on the one hand with a coupling agent, and on the other hand with a bonding agent. It is the function of a spacer to increase the distance between vehicle and bonding agent and to counteract thereby steric interference.

The term "vehicle substance" denotes a chain which consists at least of one vehicle and one bonding agent; however, the chain may be composed of a vehicle, a coupling agent, a spacer, and a bonding agent. In a chain formed in this fashion in the vehicle substance, each of the groups capable of reaction will react with a reactive group of the substances, thus forming chains. If, for example, the vehicle includes a group capable of reaction, the coupling agent for this compound must comprise a reactive group.

A "group capable of reaction" is a nucleophilic reagent, especially hydroxy- or amino-groups. A "reactive" group is a reagent group of a substance which readily enters into an addition- or condensation reaction with a group capable of reaction.

A "biologically active" substance may be a biological substance as such or a substance which is always capable of interacting with a biological substance. For example, it may be a protein, an enzyme or the like, or it may be any organic or inorganic matter constituting the substrate for an enzyme.

An "agent" is a vehicle substance containing a biologically active substance.

It is known that vehicles containing hydroxyl groups especially polysaccharides such as cellulose or dextrane and agarose, may be activated so as to enable them to bond biologically active matter containing amino groups or hydroxyl groups. For example, agarose gels may be activated with cyanogen bromide in the presence of alkali to enable them to bond proteins and other biological substances. However, the bonding effect is not stable enough. A number of bonding systems evolve, whose stability is dissimilar. The vehicle substance has to be prepared immediately prior to use, that is to say it is not storable. Several theories are held with regard to accurate conversion. No exact explanation has been offered up to now. (Methods in Enzymology, vol. 34, pp 13 to 30)

According to another, known, method, the coupling between a vehicle and a biologically active substance may be effected by means of reagents containing two or more reactive groups. For example, cellulose is activated by cyanuric chloride, the resultant vehicle substance thereby retaining chemically active chlorine groups which are capable of reacting with protein. The drawback of this method is that cyanuric chloride entails the denaturation of sensitive biologically active matter. (Nature, vol. 216, 1967, pp. 514 to 515).

It is also known that agarose can be coupled with divinyl sulfone. The resulting vehicle substance adds biologically active matter, for example, protein preserving, and the yield is good. However, bondage is very weak and the agent consequently sheds the bonded protein very quickly. (Methods in Enzymology, as quoted).

Also known is the manufacture of a vehicle substance in a reaction between agarose and Bisoxiranes. The resultant vehicle substance bonds protein under the formation of stable linkages. However, in order to effect this linkage, the pH conditions have to be extreme, and there is therefore the danger of sensitive substances such as biologically active matter being destroyed. (Methods in Enzymology, as quoted).

To bond macro molecules for the purpose of creating interaction with other macro molecules, the distance from the vehicle surface should be great enough to allow for the space required by the interaction. It is known that this distance may be bridged as required by means of suitable intermediate compounds defined as spacers. For example, it is known that agarose is activated by means of cyanogen bromide and to bond with the product a diamine of extended chain-length, which acts as a spacer. The free group is succinylated, and the carboxyl groups is activated through N-hydroxy-succinimide and dicyclohexyl carbodiimide. However, considerable chemical expenditure is necessary. Manipulation during reactions is difficult and in the case of large scale reactions it can hardly be carried out. (Biochemistry, vol. 11; 1972, 2291-99).

It is an object of the invention to synthetise a vehicle substance which permits biologically active matter to be bonded to an insoluble vehicle in such a manner that the capability of the biologically active substance of interacting with another biological substance is not affected. In particular, it is an object of the invention to present an agent which contains covalently bonded enzymes in a high yield, and which has the following properties:

(a) has a temperature resistance up to 100° C.
(b) is mechanically stable and resistant to compressive load
(c) has a low flow resistance
(d) is free from charge carriers
(e) is hydrophilic The linkage of the biologically active matter, for example, enzyme, with the vehicle, should (f) be very stable against hydrolysis in the pH range 3 to 11,
(g) affect the vehicle characteristics as little as possible,
(h) be affected under very gentle conditions (aqueous solution, neutral pH range),
(i) be carried out specifically,
(k) not interfere with enzymetic effect when coupled with the vehicle and
(l) not sterically hinder the reaction of enzymes with high molecular substances.

It is emphasized in this connection that there are certain applications where it is not necessary for all of the above listed characteristics to be reached. However, with practically all sensitive enzymes, and with enzymes having high molecular co-reactants it is important that the characteristics listed under (a) to (l) should be simultaneously present.

The method according to the invention, relating to the production of a vehicle substance, distinguishes itself in that one or preferably both reactive groups of the bonding agent are isocyanates. The method is founded on the sequence of an interrupted process, i.e., a vehicle substance being produced and if required isolated, in a first stage of the process. Even this first stage is carried out step by step, and the intermediate product obtained from each step is isolated, say by filtration. When the process is completed in one single stage, only one bonding agent is involved however, as soon as a coupling agent and a spacer are introduced, the process is divided into several stages. The numerous possibilities given when a bonding agent, a coupling agent, and a spacer are used, and their various feasible combinations enable the product to be accurately adjusted so that it has the properties required for any particular application, the vehicle substance being built up gradually and in conformity with these requirements.

The vehicle itself for example, is responsible for properties (b) to (c). The bonding agent and the coupling agent essentially determine the properties (f), (g), (h), (i), and (k). The spacer determines mainly the properties of (l). The other characteristics, which are not specifically defined, are affected by the combination of the vehicle, the bonding agent, the coupling agent, etc. Thus it is possible for the biologically active agent to be directly attached to the vehicle through the bonding agent alone. Alternatively, the bonding agent can be linked with the vehicle through spacer and coupling agent, so as to counteract steric interference and to increase the efficiency of biologically active substances which are bonded with a vehicle substance.

A vehicle may consist of natural organic substances such as cellulose, agarose, dextrane or the like. Also synthetic polymers have been tried out, for example the derivatives of acryl amide. Alternatively, the vehicle material may be an inorganic substance such as glass. When deciding on which substance to chose it is necessary to take a number of parameters into consideration. the macroscopic form of the vehicle is important. The material may for example be globular or in pearl form, or in fibre form for example be cotton wool or the like, or it may be granular. When pearl shaped particles are used, two additional parameters namely grain size and porosity are to be taken into account. Depending on the above parameters, it is feasible to make the bondage on the surface or in the inner regions of the material predominant. With coarse grain sizes, the occupation density is usually moderate. The occupation density is generally considered as a standard for the assessment of the quantity of biologically active matter which is bonded per unit volume of the vehicle substance. The porosity affects essentially the mechanical stability and resistance to compression. In cases where these properties are particularly important it is recommended to use as a vehicle substance a small-pored or non-porous material. The flow resistance of the vehicle substance depends on the macroscopic form of the vehicle substance and on the particle size.

The choice of the bonding agent and also of the coupling agent will be influenced by the desire to maintain the vehicle properties as constant as possible. Therefore the chosen material will be such that the number of secondary reactions which could adversely change the vehicle substance are as small as possible. When using isocyanate it is therefore understood that the vehicle should be anhydrous and that also the process uses no water. This means that one has to operate with organic solvents. Aprotic, polar, solvents such as cyclic ethers, for example THF (tetrahydrofurane) or dioxan have given excellent experimental results. Also aceto nitrile, dimethyl formamide, and formamide are highly suitable aprotic solvents.

Since the method uses an interrupted process and the solvent has to be removed after completion of each stage it is an advantage if the solvent has a relatively low boiling point. It should be approximately below 100° C.

The coupling agent is preferably an aromatic or aliphatic di-isocyanate. The coupling agents should be not more than slightyly hydrophobic. When operating with aliphatic di-isocyanates a short-chain di-isocyanate should be used which may be saturated or non-saturated. Aromatic di-isocyanates should have the smallest possible number of hydrophobic groups. The following di-isocyanates are especially suitable:

toluene-2,4-di-isocyanate, toluene-2,6-di-isocyanate, commercial mixtures of toluene-2,4 and 2,6 di-isocyanate, ethylene di-isocyanate, ethylidene diisocyanate, propylene-1,2-di-isocyanate, cyclohexylene 1,2-di-isocyanate, cyclohexylene-1,4-di-isocyanate, m-phenylene di-isocyanate.

Since the groups capable of reaction of numerous vehicles are slow to react, it is necessary to use a catalyst. These may be a strong bases, especially sodium imidazolide. Similarly, metallorganic catalysts of the polyurethane chemistry could be used. The charge density may be controlled by varying the quantity of the catalyst employed. The coupling- and bonding agents should always be present in excess. Frequently five to ten times the necessary quantity are present. The reaction temperature is between room temperature and the boiling temperature of the solvent used with the process. For example when the vehicle consists of microporous, pearl-shaped particles having a granular size between approximately 10 and 50 m, result will be satisfactory when the reaction is controlled in such a manner that the the charge density amounts to 25 to 200 mols per ml of the bulk volume. The reaction is completed by scrubbing the excess reagents, using an anhydrous solvent, preferably the solvent which will be used with the consequent reaction.

The spacer should be a substance containing at least two groups capable of reaction. When two groups are used, a linear chain is formed. When substances containing more than two groups capable of reaction are involved, the chain will branch out. Substances which are especially suitable for this purpose are aromatic or aliphatic saturated or unsaturated diamines, amino-alcohols, or diols. Obviously a substance used as a spacer should not contain hydrophobic groups. Saturated aliphatics having a short chain length and containing two groups which are capable of reacting, will yield good results.

If it is desirable to increase the chain length, it is advisable to use polyethylene glycols having a low molecular weight. By this method it is possible to avoid the hydrophobic effect of long aliphatic chains. Unsaturated aliphatic or aromatic diols or diamines offer the special advantage of yielding a spacer which is essentially rigid or rather moderately flexible, the advantage being that the biologically active substance which is subsequently attached to it is freely supported and thus prevented from clinging to the vehicle substance. Thus the substance cannot fold back. Analoguously, ramification is a means by which to increase the occupation density.

Numerous substances have been tested and found to provide excellent spacers. Only several preferred examples are named hereinbelow:

Diamines:
Ethylendiamine, tetramethylendiamine, 1,5-diamine-3-azapentane, m-phenylendiamine etc.

Amino-alcohols:
Ethanolamine, 1-aminobutene-2,3-ol-4,3-aminocyclohenxanol, p-aminophenol etc.

Diols:
Ethyenglycol, glycerol, butanediol-1,4: 2-2-butene-2,3-diol-1,4, 1,4,-hydroquinone, resorcin, phloroglucinol etc.
Polyethylenglycol fractions having a low molecular weight.

In order to ensure that only one of the groups capable of reacting which are contained reacts with the coupling agent, the spacer substance is present in a high excess, preferably 10 times. It is normally possible to operate in the absence of a catalyst. However, a weak base such as tri-ethylamine may be used. The solvents, temperature and scrubbing of the reaction products specified above apply analogously to the spacer reactions. When using a spacer it is necessary to insert a bonding agent between the spacer and a biologically active substance. Again, the bonding agent should contain two reactive groups. The same substances which were specified above as suitable coupling agents may advantageously be used as bonding agents. Regarding the choice of the coupling agent, analogous criteria are to be considered. However, since the groups capable of reacting which were used with the spacer are less inert than the groups capable of reacting which are contained in the vehicle, it is possible for a catalyst to be chosen which causes the bonding agent to react exclusively with the spacer. Catalysts suitable for these reactions are aprotic, weak bases such as triethylamine. Again, the reaction takes place place in the presence of a high excess. The information given above in respect of solvents, temperature and isolation apply analogously. The scrubbing of excess substances is followed by the evaporation of the solvent so that the vehicle substance is obtained for example in powder form in which it may safely be stored. The vehicle substance includes at its end an isocyanate group. This is not, however, an absolutely necessary condition. The end might equally well be a deactivation agent which enables the end to dissolve again when a biologically active substance is attached. Compounds having these characteristics have been defined as "isocyanate in disguise". The deactivation agent is introduced in solution in an organic solvent. Again the product may be isolated and stored.

When coupled with biologically active substances the deactivation agent is exchanged against the biologically active substance. Suitable desactivation agents are, theophenols, phenol derivatives, for example 2,4dinitrophenol, hydroxyl amine derivatives such as N-hydroxysuccinimide, cyclic amines for example benzimidazol or similar substances.

The reactive mechanism demonstrated in the example of isocyanate and di-isocyanate may of course be extended over other coupling agents and bonding agents. Further reactive groups which could be used as bonding agents or coupling agents, are acyl halogenides, activated esters, iso-thiocyanates, sulphonic chlorides, chloroformates, and similar substances.

The coupling of biologically active substances is extremely simple. The vehicle substance is stirred into the solution of the biologically active substance in a suitable solvent. The charge density can be enhanced to an especially high level by using biologically active substances which are soluble in aprotic organic solvents. There are no secondary reactions. This applies especially to certain classes of material such as antibiotics. Enzymes and other proteins are normally used in aqueous solution. The secondary reaction which occurs in this case is the hydrolysis of the isocyanate. However, the amino groups in the biologically active substance react with isocyanate much more rapidly than the water which means that even with these reactions a high occupation density may be produced. The solution of enzymes and other proteins in water must be buffered. Any buffer substance which is free from groups capable of reacting is suitable. Good results have been obtained with phosphate buffers imidazol buffers, and Good's buffer solutions. The pH range should be neutral or slightly alkaline. Good results have been reported from solutions with pH range 6 and 10. The bonding reaction is carried out at room temperature or in the cold. Once established, the bond is very firm. All enzymes examined were found to be free from leakage. The resulting vehicle substance including the biologically active material is free from additional ionic groups.

Approximately 20 enzymes were bonded with a vehicle material. Because of their considerable sensitivity some of these have previously resisted all attempts of immobilisation.

All enzymes examined in this connection were bonded in their active form with the vehicle substance. This seemed to indicate a definite probability of the method being generally applicable.

Again, the coupling agent may be a bonding agent with two reactive groups, and isocyanate may constitute one or preferably both of the reactive groups. Alternatively, di-isocyanate could serve as the bonding agent and as the coupling agent, and the spacer could be composed of a substance with at least two groups which are capable of reacting, such as especially amino and/or hydroxyl groups. The corresponding links are always stable.

To increase the occupation density it is moreover feasible that two or more di-isocyanates, employed as bonding agents, are bonded with the coupling agent through a substance containing at least three groups capable of reaction especially amino- and/or hydroxyl groups.

In certain cases of application it is good policy to reduce the reactivity of the isocyanate group of the vehicle substance using a deactivation agent in order to arrive at a specific bonding effect. This is particularly advantageous when proteins or enzymes in an aquaeous solution are bonded with vehicle matter, because this reduces the rate of hydrolysis of the isocyanate considerably.

The proposed method enables activated vehicle substances to be manufactured in large quantities, using commercially produced cheap chemicals. In the anhydrous state, the activated vehicle substances are stable, and they bond covalently biologically active matter containing free -NH$_2$ or -OH-groups, in water or in organic solvents. The biological activity of the substance is retained during the bonding process, the vehicle substance causing steric interference of the biological activity is effectively averted by the intermediate coupling of spacers. The covalent linkage is chemically stable. The properties of the vehicle, especially its porosity, flow rate, and melting temperature are not affected by the method of activation. The method is particularly favourable where immobilised enzymes are produced, and it yields agents which are particularly valuable in flow reacters.

It is characteristic for vehicle substances for the immobilisation of biologically active matter especially enzymes, that they have at least one reactive group and that this reactive group is an isocyanate group. Conditions are particularly favorable for the optimum efficiency of the biologically active material which is later linked, when the reactive isocyanate group is linked with the vehicle through a spacer, a coupling agent being provided between the spacer and the vehicle. This coupling agent may be a bonding agent with two reactive groups, whereby isocyanate is preferentially employed as one, or both, of the reactive groups. When isocyanates react with groups capable of reaction, one obtains exclusively substituted urethane, or substituted urea.

The agent according to the invention containing biologically active matter which is immobilised by means of a vehicle substance is distinguished by a substituted urea resulting from the linkage of an amino group between the biologically active matter. Alternatively a hydroxyl group of the biologically active matter could be linked with the vehicle substance into a substituted urethane to convert the isocyanate group. Also in this case, the vehicle substance is distinguished by one or several of the characteristics described above.

Figure 1:
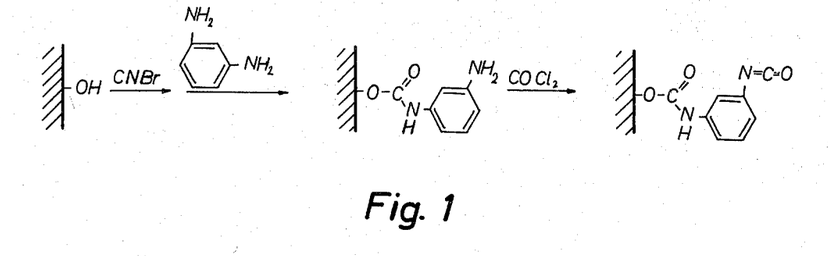

The examples for vehicle substances and agents which follow below illustrate the importance of the invention:

(1a) Examples for the synthesis of vehicle substances capable of bonding biologic matter, and using isocyanate groups:
  (a) the isocyanate group provides the link with the vehicle: a vehicle, for example cellulose, is activated with cyanogen bromide and converted with the aid of phenylenediamine. The resulting compound reacts with phosgene, forming isocyanate which in turn reacts with the biological matter. (See FIG. 1)

Figure 2:
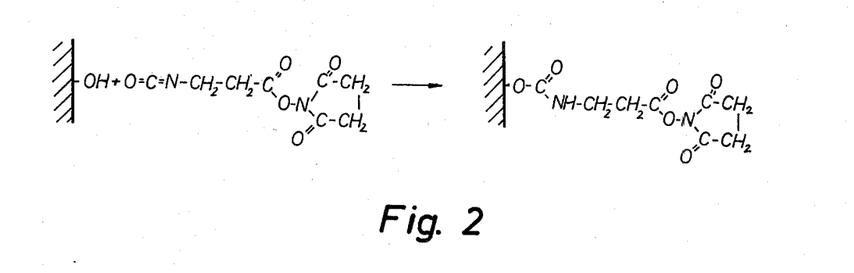

(1b) The link between vehicle and biological material is provided by the isocyanate group: Agarose, acting as a vehicle, is reacted with a bonding agent which contains both a isocyanate group and an activated ester. The isocyanate group combines with the vehicle, and the activated ester group is able to condense with the biological substance, (See FIG. 2).

Figure 3:
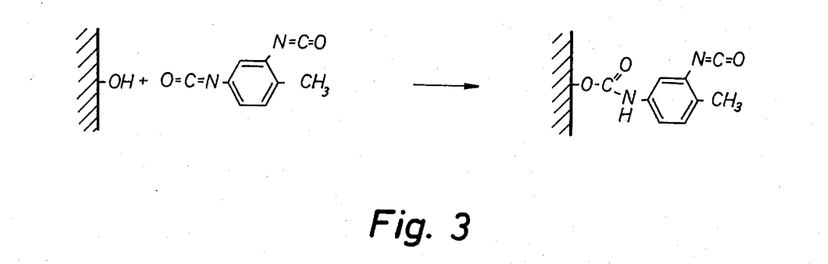

(1c) Both reactive groups of the bonding agent, are cyanate groups that is to say the bonding agent is a di-isocyanate. (See FIG. 3).

Figure 4:
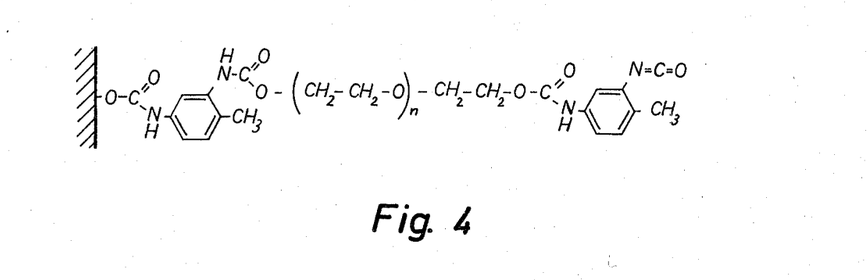

(2a) Example for a vehicle substance of consisting of vehicle, coupling agent, spacer, and bonding agent: All reactive groups in the chosen example, whether in the bonding agent or in the coupling agent, are isocyanate groups. A hydrophilic compound having an extended chain length, acts as a spacer. Cellulose, constituting the vehicle, is converted in the presence of the strong base sodium imidasolide, with toluene diisocyanate and the resultant compound adds, as spacer, n-polyethyleneglycol. In a further reaction with toluene di-isocyanate in the presence of the weak base tri-ethylamine, the bonding agent reacts with the primary OH-group of the spacer, while residual secondary hydroxyl groups of the vehicle no longer react; thus the following substance evolves. (See FIG. 4).

Figure 5:
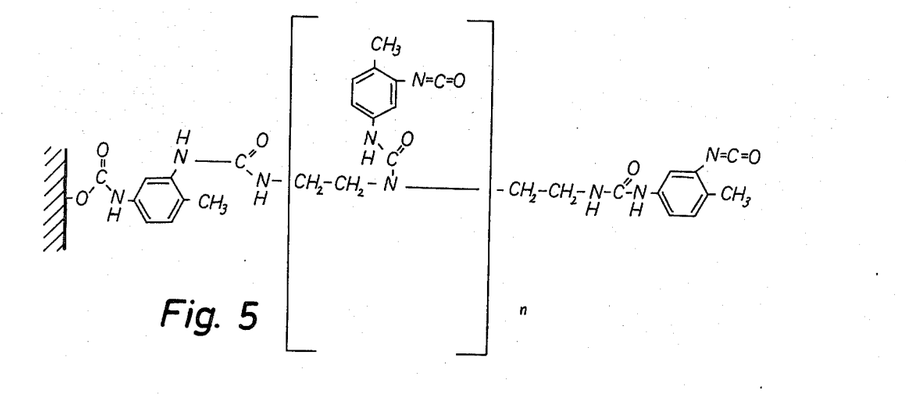

(2b) Example for ramification caused by a polyamino compound: Reaction as (2a), excepting the spacer which now is a polyethyleneimine. (FIG. 5).

Figures 6, 7:
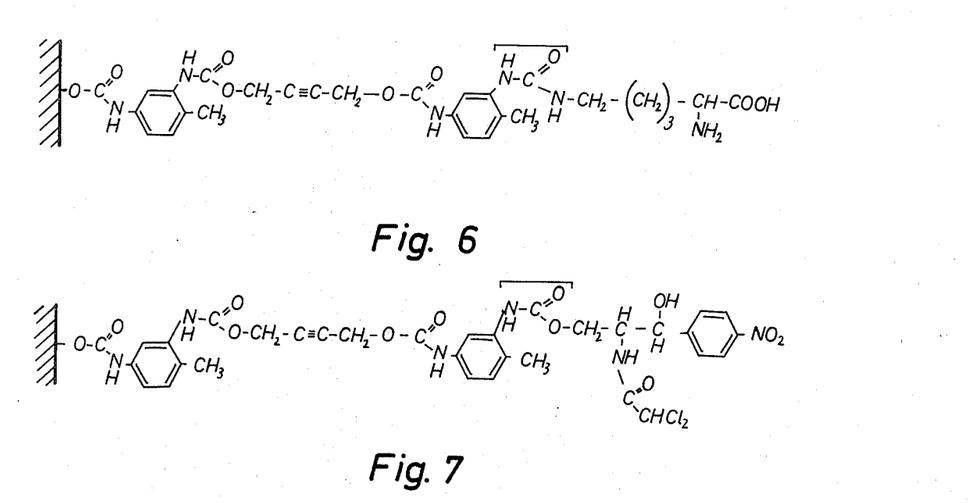

(3a) Example for bondage of urea between a vehicle substance carrying isocyanate groups, and a biological substance containing amino groups: A vehicle substance, for example the agent resulting from the reaction according to (2a), reacts in aqueous solution with lysin forming a substituted urea (FIG. 6). Enzymes containing lysin react in the same manner.

(3b) Examples for urethane bondage between a vehicle substance containing free isocyanate groups and a biological substance containing free hydroxyl groups: A substance as described in examples (2a) or 2b) is reacted with chloramphenicol in diozane, whereby the following compound evolves (FIG. 7).

Figure 8:
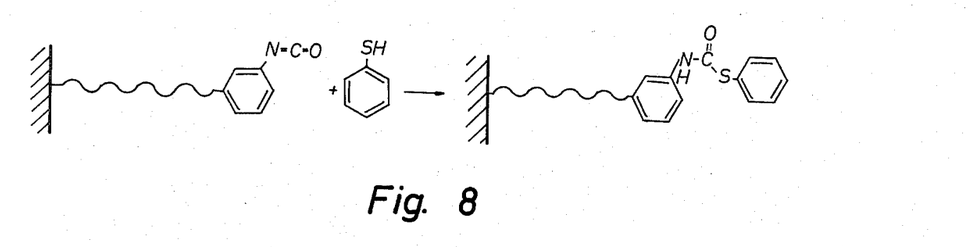

(4) Example for a deactivation:
A vehicle substance containing free isocyanate groups is reacted with thiophenol in organic solutions (FIG. 8).

(5a) Vehicle Substance Prepared from Dextrane Gels.
  5 g of dried Sephadex G 50 superfine (Pharmacia; microporous, cross-linked dextrane gel) are suspended in 100 ml anhydrous tetrahydrofuran (THF). While stirring, 1 ml of toluene di-isocyanate (commercial mixture of 2,4 and 2,6 isomers) and 0.5 ml of a catalyst in suspension are added, followed by heating to the reflux temperature under rigorous stirring for 30 mins. The suspension is filtered off and scrubbed with anhydrous THF to remove excess reagents.

The pearls are suspended in a solution of 2 g 2-Butyne-1,4-diol in dry THF, and heated for 30 mins to reflux. The substance is extracted and carefully scrubbed with anhydrous THF, after which the solvent is removed in the vacuum, and the product is sealed in vials. When examined after storage for several months, no decrease in the bonding capacity was detected.

The yellow pellets swell in water like the initial substance; similarly, the appearance and flow resistance are the same.

Isocyanate concentration: 250 $\mu$Moles/g

Lysine bonding power in aqueous solution: 4 $\mu$Moles/g

Bondage of enzymes to the vehicle substance in accordance with 5a.

Alkaline Phosphatase from *E. coli* (Boehringer, 200 g) is dialysed against 0.2 M phosphate buffer (pH 8,0) and the volume of the enzyme solution is increased to 400 μl. The enzyme solution is mixed with 10 mg of the vehicle substance according to 5a, and the solution is left standing for 2 hours under slight stirring, followed by shaking. 100 μl of the suspension are packed into a small column (diameter of the column 22 mm, bed-volume of substance 10 μl). This column is scrubbed with 0.05 H tris-buffer (pH 7.5) followed by equilibration with substrate solution (0.05 M glycine buffer, (pH 10.5), 5.5 mm p-nitrophenyle phosphate, 0.5 mM $MgCl_2$), The flow rate is adjusted at 4 secs. per column volume, fractions being collected continuously. The reaction should adjust itself to a steady state within a few seconds. The activity is calculated from this level. 1 g of the agent has the activity of 1.3 mg free enzyme. Secondary incubation of the collected fractions, maintained for several hours, enables the contamination to be measured with detached enzyme. Such contamination is immeasurably small.

After standing at room temperature for one week in a glycine buffer (pH 10.5), it was found that the activity of the agent had not diminished.

Lysine Bondage Standard text: 1 mM lysine in 0.2 M of a buffer of potassium phosphate, 50 mg vehicle substance per 1 ml solution. After reaction time of 1 hour at 4° C., the fixation of the radioactive lysine is measured. Fixation of lysine when using other buffer conditions:

| Standard condition | 100% |
|---|---|
| 0.02 M Phosphate pH 8.0 | 135% |
| 0.02 M Phosphate pH 6.7 | 48% |
| 0.05 MEPES pH 7.4 | 80% |
| 0.05 Imidazol pH 8.0 | 90% |

With neutral pH conditions, the resulting agent does not act as an ion-exchanger. Measurements are taken of the amount of bound radioactive ADP by the lysine substance. One g of the agent binds less than 1 p Mol ($10^{-12}$ Mol) ADP.

Using standard conditions, the following enzymes are bonded in their active form with the vehicle substance:

Trypsin inhibitor from soya beans (Merck). The product has a reversible bonding capacity of 3.1 mg Trypsin/g.

Lactate dehydrogenase from pigs muscles (Boehringer) The activity of the product is too high for an accurate measurement of the surface density (50 E/g) to be carried out.

Apyrase from potatoes (Sigma)
Urease from Jack beans (Boehringer)
Diaphorase (Sigma)

The standard conditions are: 50 g of the vehicle substance are mixed with the solution of 10 mg enzyme in 1 ml of an 0.2 M phosphate buffer (pH 8.0), and the suspension is incubated for 2 hours at 4° C., under occasional shaking. At least ⅔ of the excess enzyme activity are recovered for use in subsequent bonding reactions.

(5b) Example for the use of polyethylene glycol as a spacer, the vehicle being dextrane gels. The production of the vehicle substance from Sephadex is analoguous to the example described above. However, the spacer solution is replaced by a solution of 20 ml polyethylene glycol 200 in 200 ml THF.

The obtained product is very similar to the above; however, the bonding capacity is usually below that of the previous example, the lysine bonding capacity for example being 5.6 μMol/g, and the activity of the bonded lactate dehydrogenase amounting to 16 units/g.

(6a) Vehicle Substance Made from Granular Cellulose.

(Cellulose for thin-layer chromatography (Merck) native, granulate).

2.5 g cellulose are vacuum-dried, and floated in a solution of 0.5 ml TDI and 0.375 catalyst suspension in 150 ml THF, followed by heating the reflux for 30 minutes under stirring. The product is added to a solution of 2 g butine diol in 150 THF and heated to reflux for 30 mins. It is again scrubbed and filtered, and the cake is floated in a solution of 2.5 TDI and 0.25 ml triethylamine in 150 ml THF. The substance is extracted, thoroughly scrubbed in anhydrous THF and dried in the vacuum.

Characteristics: fine granulate, yellowish in colour.

Lysine bonding power in aqueous solution: 4.5 μMol/g.

Enzyme bondage with a vehicle substance according to 6a. Bondage takes place under conditions described above.

Trypsin The activity of 1 g of the agent is equivalent to 1.8 mg enzyme.

Polynuleotide phosphorylase A partially enriched enzyme fraction of *E. coli*. The activity of 1 g of the substance is equal to 0.8 mg of the preparation. Measured was the formation of high polymer, poly-U from UDP. In a continuous process, the half life amounts to approximately 14 days. This means that after a reaction period of 14 days the throughput of a flow reactor which is in continuous operation at room temperature, drops to half the original value. The quantity dealt with during this period is about 10,000 column volumes. Since no traces of enzymes were found in the runs, the decrease is attributed to denaturation or desintegration of the enzyme into its sub-units.

RNA Polymerase, a partially enriched preparation from *E. coli*. The synthesis of poly-AU on a high-molecular matrix of poly dAT was measured. The stability of the bonded enzyme amounted to a multiple of the stability of free enzymes. The activity of 1 g of the agent is equivalent to 0.12 mg of the free enzyme.

Guanylate Kinase, A partially enriched crude fraction from *E. coli*. The column is suitable for enzymatic synthesis of GDP and GTP and it is especially favourable for the synthesis of radioactively marked GDP, GTP, IDP and ITP.

Nucleoside diphosphate Kinase, a partially enriched protein fraction from *E. coli*. The agent is suitable for the synthesis of phosphate labelled nucleoside- and desoxynucleoside triphosphates.

Diphospho-kinase and Polynucleotide Phophorylase. Partially enriched protein fractions from *E. coli* are mixed followed by bonding. In the case of nucleoside tri-phosphates and nucleoside di-phosphates the agent exchanges specifically the β-phosphate against added, radioactive phospahte.

Prostatic, Acid Phosphatase, a partially enriched protein fraction from human semen. The immobilised crude enzymes mentioned above are excellently suited for the production of substrates for the synthesis of nucleic acid. In free solution, these crude enzymes are unsuitable for this production because nucleases and other degrading enzymes contained as impurities in the crude enzymes cannot be removed from the substrate preparation or only at the cost of considerable expenditures. By using bonded enzymes, the problem of concentration be bypassed provided that the bonded enzyme remains present as a stable bond instead of being gradaully washed away from the reactor. When the means specified in the description of this method are applied there is no danger of it losing the stability.

Ribonuclease, made from pancreas. This substance degrades completely high molecular poly-U into 3'-UDP, and breaks tRNA up into the typical oligo nucleotide mixture. No steric interference has been observed. The charge density is high.

(6b) Preparation of a vehicle substance of cellulose wool.

The manufacture corresponds to example 6a, the difference being that surgical cotton wool (2 g) constitutes the vehicle. Characteristics: the external appearance the cotton wool remains unchanged except for a slight yellowing. The lysin bonding capacity in aqueous solution is 0.75 $\mu$Mol/g. The bondage of enzymes is as specified in example 6a. The charge density, however, is lower; this is due to the relatively small surface of the vehicle. The vehicle material offers advantages in reactions of highly viscous solutions: for example, when cracking high molecular DNA by means of DNases, or during the synthesis of high molecular poly A, using polynucleotide phosphorylase.

(7) Preparation of Vehicle Substance, Using Agarose.

Agarose which was allowed to swell cannot be dried without destruction of the gel structure. Consequently, the water has to be removed by means of a suitable solvent. 100 ml (sedimentation volume) Sepharose 4 B (macroporous 4% agarose gel in form of pearls, Pharmacia) is throughly scrubbed with dried dioxane. The last traces of moisture are removed by allowing the dioxane suspension to stand for at least 24 hours over a molecular sieve. The volume of the suspension is increased to 150 ml by the addition of dioxane, after which 2 ml of toluene di-isocyanate-2,4 and 1 ml catalyst suspension are added. The suspension is slowly stirred for 30 mins. at room temperature, followed by filtering and by scrubbing with dioxane. The substance must not be dried by rapid water extraction. The cake is floated in 100 ml dioxane, and 10 g butine diol-1,4 are added. After stirring for 1 hour, the product is again filtered and scrubbed. The substance is added to a solution of 10 g toluene di-isocyanate and 1 ml triethylamine in 100 ml dioxane, and gently stirred at room temperature for 30 mins. The gel pearls are carefully scrubbed and vacuum dried.

Properties of the substance: yellow pearl shaped pellets: swelling capacity and pore size are reduced by cross-linkage. Mechanical strength and melting temperature considerably increased. No change to be noticed in the gel structure when heated to 65° C.; The drying process has not an appreciable effect on the gel structure. When stored in the absence of humidity the bonding capacity does not decrease during periods of several months.

Lysine bonding capacity in aqueous solution: 10 Mol/g.

Haemoglobin bonding capacity: 230 mg/g.

Biological Substances bonded with vehicle materials according to example 7

Trypsin inhibitor from soya beans (Merck)

1 g of the agent absorbs and desorbs specifically 18.6 mg of trypsin. The capacity is not reduced by repeated use of the agent. The following, highly sensitive enzymes which catalyse the synthesis of high molecular nucleic acids bond successfully with the vehicle substance according to example 7, and are suitable for use in flow reactors.

DNA Polymerase, a highly enriched preparation from E. coli.

RNA Polymerase, a homogeneous preparation made from E. coli.

Polynucleotide Phosphorylase, a highly enriched preparation from E. coli.

RNA Replicase, a homogeneous preparation made from E. coli cells, which are infected by means of the $Q\beta$ Phage. The stability of the immobilised enzymes reaches a multiple of the stability of enzymes in solution.

Rifampicin. Antibiotics are best bonded in organic solvents. 5 g of a vehicle substance according to example 7 are floated in a solution of 50 mg Rifampicin and 0.1 ml triethylamine in 100 ml dry dioxane. After slow stirring over night, at room temperature, the agent is extracted and thoroughly scrubbed with water. The reddish brown product is stored in the form of an aqueous suspension. No appreciable quantities of Rifampicin have been found to be lost after storage for several months. The agent adsorbs specifically RNA-polymerase.

(8a) Preparation of a vehicle substance from polyacrylamide.

10 g BioGel P 10 (microporous pellets (pearls), 100 to 200 mesh, BioRad Labroatories) are allowed to swell in 100 ml hydrazine hydrate, and heated for 3 hours to 80° C. Subsequently, the product is thoroughly scrubbed with water and the gel pellets are floated in ice-cold 0.5 HCl, to be titrated at 0° C. with 0.5 M $NaNO_2$ solution (indicator: iodized starch paper, 185 ml $NaNO_2$ solution was required). The gel is extracted and quickly scrubbed in ice cold water. Subsequently the gel is floated in 100 ml of a 10% solution of polyethylenimine (in water) and left standing over night. During this period, polyethylenimine is bonded with the surface, and yields the groups capable of reaction which are required by the consequent reactions. The product is scrubbed first with water and then with alcohol and dried in the vacuum. Any lumps are pulverised in order to obtain a uniformly fine powder.

The vehicle substance modified as specified above is floated in 100 ml dioxane and mixed with 2 ml toluene di-isocyanate. The product is stirred for 30 minutes while heated to 40° C., and subsequently filtered and scrubbed with dioxane. The resulting substance is floated in a solution of 2 g butine diol-1,4 in 100 ml dioxane and heated to 40° C., while stirring for 30 minutes. The product is extracted, scrubbed with dioxane, and floated in a solution of 5 ml toluene di-isocyanate in 100 ml dioxane. After heating to 50° C. for 30 min, (in the absence of a catalyst) the product is filtered, scrubbed, and dried.

Properties: fine, microporous, pearls which slightly swell in water.

Capacity of lysine bondage in aqueous solution 17.6 Mol/g

Haemoglobin bondage in buffer solution 14.8 mg/g.

(8b) Deactivation of the vehicle substance:

100 mg each of the above vehicle substance of polyacrylamide are floated in a solution of 10 mg deactivation agent in 2 ml dioxane, and shaken for 30 mins. at room temperature. The deactivated substances are filtered off, scrubbed with dioxane, and dried.

The capacity of haemoglobin bondage of deactivated vehicle substances are listed below:

| In the absence of a deactivation agent | 100% |
|---|---|
| nitro-phenol-4 | 114% |
| di-nitrophenol-14 | 116% |
| thiophenol-4 | 87% |
| N-hydroxysuccinimid | 109% |
| N-Hydroxypiperidin | 121% |
| Benzimidazol | 115% |

(9) Preparation of a vehicle substance of porous glass.

4 g of controlled pore glass pellets (macroporous pearls, pore size 900 Å) are mixed with 100 ml. of a 1% solution of γ-aminopropyl triethoxysilane in acetone. The acetone is removed at partial vacuum and moderate heat, in a rotating evaporator. The residue is incubated over night at 115° C. This known preliminary reaction makes the groups capable of reaction available which are required for the consequent reactions. The product is mixed with 100 ml of a 2% solution of tetramethylene di-isocyanate and allowed to react in the absence of a catalyst at room temperature, for 30 mins. The product is extracted, scrubbed, and converted with 100 ml of a 5% solution of anhydrous phloroglucinol in THF. It is again filtered and scrubbed before being converted with 100 ml of a 5% solution of toluene di-isocyanate, in THF. The final product is scrubbed, and dried.

Bonding of enzymes or other proteins (e.g. antibodies) occurs under the conditions specified above.

Example for the application of vehicle substances in the manufacture of chromatigraphic materials: The vehicle substance described above is reacted in a solution of 3-aminophenyle boronic acid in a polar, aprotic, organic solvent. The resultant substance is suitable for the chronotography of sugars, nucleosides, and nucleotides in aqueous solution.

The above described examples are carried out in the presence of a catalyst which could be prepared, for example, as follows: Equimolar quantities of sodium and imidazol are reacted into sodiumimidazolide, using anhydrous toluene in a known manner. The suspension is adjusted to approximately 1 Mol/liter. Preferred applications are:

(1) Vehicle-bonded enzymes for use as flow reactors. Their favorable values of temperature and stability under compression make modified dextrane or cellulose preferable, which do not denature enzymes, the preferred vehicle. Experiments were carried out with numerous enzymes. All tested enzymes possessed, activity was high enough to suit the conditions of high flow rates. In the majority of cases, the stability of immobilised enzymes was found to be very great. No traces of residual enzymes were detected in the reaction products.

(2) Vehicle-bonded proteins, oligonucleotides, amino acids, antibiotics or other biological substances as agents in the affinity-chromatography of enzymes. It is on account of its high bonding capacity (large pore width) that agarose is the preferred vehicle, all the more so since it is not necessary to display a high flow rate and a high temperature stability.

(3) Various chemical groups are introduced into column substances, for example when producing ion exchangers or other chromatographic material.

The attainable capacity is very great and there is no need for spacers to be used with this material.

What is claimed is:

1. In a method for the production of a vehicle substance capable of covalent bonding with a biologically active matter which is synthetized from a vehicle containing preferably several free —NH$_2$ or —OH groups and at least a bonding agent containing at least two reactive groups, the improvement wherein the vehicle under anhydrous conditions is reacted with an excess of organic diisocyanate in an anhydrous organic aprotic solvent in the presence of a strong basic catalyst, and the resultant vehicle substance is isolated in a storable form.

2. A method according to claim 1, characterized in that the bonding agent is bonded with the vehicle via a spacer and a coupling agent.

3. A method according to claim 2, characterized in that a substance containing at least two reacting groups constitutes the spacer.

4. A method according to claim 2, characterized in that a bonding agent having two reactive groups constitutes the coupling agent, and isocyanate or capped isocyanate constitutes one or preferably both reactive groups.

5. A method according to claim 2, characterized in that a diisocyanate or a capped diisocyanate constitutes the bonding agent and the coupling agent and the spacer is formed from a substance with at least two reactive groups, especially amino and/or hydroxyl groups.

6. Process according to claim 5, characterized in that for increasing of the coating density, two or more diisocyanates or capped diisocyanates used as bonding agents are bonded to a coupling agent via a substance having at least three reactive groups, especially amino- and/or hydroxyl groups.

7. A method according to claim 1, characterized in that for achieving a specific bonding the reactivity of the isocyanate group or of the capped isocyanate group of the vehicle substance is decreased by using a deactivation agent.

8. A method according to claim 1 wherein said vehicle is agarose, dextrane, or a derivative of acrylamide.

9. A method according to claim 1 wherein said vehicle is cotton wool in fiber form.

10. A method according to claim 1 wherein said vehicle comprises a small-pored or non-porous material.

11. A method according to claim 1 wherein said anhydrous organic aprotic solvent has a boiling point no greater than about 100° C.

12. A method according to claim 11 wherein said solvent is selected from the group consisting of tetrahydrofurane, dioxan, aceto nitrile, dimethyl formamide, and formamide.

13. A method according to claim 1 wherein said strong basic catalyst is sodium imidazolide.

14. A method according to claim 1 wherein said strong basic catalyst is selected from the group consisting of metallorganic catalysts of polyurethane chemistry.

15. A method according to claim 1 wherein said excess of organic diisocyanate is in a range of 5–10 times the necessary quantity.

16. A method according to claim 1 wherein the reaction is carried out at a temperature between room temperature and the boiling temperature of the solvent.

17. A method according to claim 1 wherein the vehicle comprises microporous, pearl-shaped particles having a granulur size between about 10 and 50 μm, and the reaction is controlled in such a manner that the charge density amounts to 25 to 200 mols per ml of the bulk volume.

18. A method according to claim 2 wherein said spacer is a diamine, an amino-alcohol, or a diol, not containing hydrophobic groups; and said coupling agent is an aromatic or aliphatic diisocyanate which is not more than slightly hydrophobic.

19. A method according to claim 18 wherein said coupling agent is a short-chain aliphatic diisocyanate or an aromatic diisocyanate having few hydrophobic groups; and said spacer is a saturated aliphatic compound having short-chain length.

20. A method according to claim 2 wherein said spacer comprises a polyethylene glycol having a low molecular weight.

21. A method according to claim 2 wherein said spacer is an unsaturated aliphatic or aromatic diol or diamine.

22. A method according to claim 2 wherein said coupling agent and said spacer are both present in a large excess.

23. A method according to claim 1 wherein said vehicle is microporous, cross-linked dextrane gel, said anhydrous organic aprotic solvent is tetrahydrofurane and said bonding agent is toluene diisocyanate, and wherein said reaction is carried out by mixing the ingredients in the presence of said catalyst, followed by heating to the reflux temperature under rigorous stirring, followed by filtration and scrubbing with anhydrous tetrahydrofurane to remove excess reagent; and wherein the resultant product is then reacted with 2-butyne-1,4-diol in anhydrous tetrahydrofurane.

24. A method according to claim 2 wherein said vehicle is dextrane gel, said process first involving the reaction in the presence of a said anhydrous organic aprotic solvent in the presence of said strong basic catalyst of a diisocyanate with said dextrane gel; then, in a second stage, reacting the product of the first stage with polyethylene glycol in an anhydrous organic aprotic solvent.

25. A method according to claim 2 wherein, in a first stage, said vehicle comprising cellulose granules normally used for thin-layer chromatography are reacted with TDI as a said coupling agent in a said anhydrous organic aprotic solvent; in a second stage, the product of the first stage is added to a solution of butine diol as said spacer in an anhydrous organic aprotic solvent to effect reaction under reflux; and, in a third stage, the product of the second stage is reacted with TDI in a said anhydrous organic aprotic solvent.

26. A method according to claim 2 wherein said vehicle is cellulose wool or agarose and wherein, in a first stage, said vehicle is reacted in the presence of said strong basic catalyst and in said anhydrous organic aprotic solvent with a bonding agent which is diisocyanate; in a second stage, the product of the first stage is reacted in a said anhydrous organic aprotic solvent with said spacer which is diol; and in a third stage, the product of said second stage is reacted in a said anhydrous organic aprotic solvent with a said bonding agent which is a diisocyanate.

* * * * *